United States Patent
Kleiner (10) Patent No.: US 8,147,744 B2
(45) Date of Patent: Apr. 3, 2012

(54) METHOD OF MAKING A STENT FORMED FROM CROSSLINKED BIOABSORBABLE POLYMER

(75) Inventor: Lothar W. Kleiner, Los Altos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 299 days.

(21) Appl. No.: 12/422,143

(22) Filed: Apr. 10, 2009

(65) Prior Publication Data

US 2010/0262223 A1    Oct. 14, 2010

(51) Int. Cl.
*B29C 49/00* (2006.01)
*B29C 35/08* (2006.01)

(52) U.S. Cl. ......................... 264/459; 264/494

(58) Field of Classification Search ................ None
See application file for complete search history.

(56) References Cited

U.S. PATENT DOCUMENTS

| | | | | |
|---|---|---|---|---|
| 6,093,463 | A * | 7/2000 | Thakrar | 428/36.9 |
| 7,241,455 | B2 * | 7/2007 | Richard | 424/423 |
| 2008/0014244 | A1 | 1/2008 | Gale et al. | |
| 2008/0015686 | A1 * | 1/2008 | Gale et al. | 623/1.38 |
| 2008/0233168 | A1 * | 9/2008 | Cheng et al. | 424/423 |

OTHER PUBLICATIONS

U.S. Appl. No. 12/415,841, filed Mar. 31, 2009, Wang.

Mitomo et al., "Improvement of heat stability of poly(L-lactic acid) by radiation-induced crosslinking", Polymer 46, pp. 4695-4703 (2005).
Parrish et al., "Functional Polyesters Prepared by Polymerization of α-Allyl(valerolactone) and its Copolymerization with ε-Caprolactone and σ-Valerolactone", J. of Polymer Science: Part A: Polymer Chemistry, vol. 40, pp. 1983-1990 (2002).
Parrish et al., "PEG-and Peptide-Grafted Aliphatic Polyesters by Click Chemistry", J. Am. Chem. Soc. 127, pp. 7404-7410 (2005).
Quynh et al., "Properties of a Poly (L-lactic acid)/Poly(D-lactic acid) Stereocomplex and the Stereocomplex Crosslinked with Triallyl Isocyanurate by Irradiation", J. of Applied Polymer Science, vol. 110, pp. 2358-2365 (2008).
Quynh et al., "Properties of crosslinked polylactides (PLLA&PDLA) by radiation and its biodegradability", EU Polymer J. 43, pp. 1779-1785 (2007).
Schüll et al., "Syntehsis and Characterization of Novel Allyl Functionalized Poly (L-Lactide)s" Research Project, Univ. of Mass. Amherst, 13 pgs. (2009).
Van Vlack, "Deformation and Fracture", Elements of Materials Science and Engineering, 4 pgs. (1989).

* cited by examiner

*Primary Examiner* — Monica A Huson
(74) *Attorney, Agent, or Firm* — Squire Sanders (US) LLP (57) ABSTRACT

A stent having a stent body made from a crosslinked bioabsorbable polymer is disclosed. A method of making the stent including exposing a tube formed from a bioabsorbable polymer to radiation to crosslink the bioabsorbable polymer and forming a stent body from the exposed tube is disclosed. The tube can include a crosslinking agent which induces crosslinking upon radiation exposure. Additionally or alternatively, the bioabsorbable polymer can be a copolymer that crosslinks upon exposure to radiation in the absence of a crosslinking agent.

22 Claims, 1 Drawing Sheet

FIG. 1

METHOD OF MAKING A STENT FORMED FROM CROSSLINKED BIOABSORBABLE POLYMER

BACKGROUND OF THE INVENTION

1. Field of the Invention

This invention relates to methods of manufacturing polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts.

Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success. Stent are also used widely in endovascular applications, such as in the popliteal artery.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength describes the external pressure that a stent is able to withstand without incurring clinically significant damage. Additionally, a stent should be sufficiently rigid to adequately maintain its size and shape throughout its service life despite the various forces that may come to bear on it, including the cyclic loading induced by the beating heart. For example, a radially directed force may tend to cause a stent to recoil inward. Furthermore, the stent should possess sufficient toughness or resistance to fracture from stress arising from crimping, expansion, and cyclic loading.

Some treatments with implantable medical devices require the presence of the device only for a limited period of time. Once treatment is complete, which may include structural tissue support and/or drug delivery, it may be desirable for the stent to be removed or disappear from the treatment location. One way of having a device disappear may be by fabricating the device in whole or in part from materials that erode or disintegrate through exposure to conditions within the body. Thus, erodible portions of the device can disappear or substantially disappear from the implant region after the treatment regimen is completed. After the process of disintegration has been completed, no portion of the device, or an erodible portion of the device will remain. In some embodiments, very negligible traces or residue may be left behind. Stents fabricated from biodegradable, bioabsorbable, and/or bioerodable materials such as bioabsorbable polymers can be designed to completely erode only after the clinical need for them has ended.

However, there are potential shortcomings in the use of polymers as a material for stents. For example, the mechanical properties and other properties are susceptible to degradation during processing.

SUMMARY OF THE INVENTION

Various embodiments of the present invention include a method of fabricating a stent, comprising: forming a tube comprising a bioabsorbable polymer, wherein the bioabsorbable polymer crosslinks when exposed to radiation; exposing the bioabsorbable polymer to radiation sufficient to crosslink the bioabsorbable polymer; and forming a stent body from the exposed tube comprising the crosslinked bioabsorbable polymer.

Additional embodiments of the present invention include a method of fabricating a stent, comprising: forming a tube comprising a bioabsorbable polymer, wherein the bioabsorbable polymer crosslinks when exposed to radiation; forming a stent from the tube; and exposing the stent to radiation sufficient to crosslink the bioabsorbable polymer.

Further embodiments of the present invention include a stent comprising a stent body for supporting a vascular lumen, wherein the stent body comprises a crosslinked bioabsorbable polymer formed from crosslinking a bioabsorbable polymer, wherein the crosslinks are between different functional groups of the bioabsorbable polymer that are not linked by a crosslinking agent that is distinct or separate from the polymer prior to crosslinking.

Other embodiments of the present invention include a stent comprising a stent body for supporting a vascular lumen, wherein the stent body comprises a crosslinked bioabsorbable polymer formed from crosslinking a bioabsorbable polymer, wherein the crosslinks are formed from a crosslinking agent that links functional groups of the bioabsorbable polymer when exposed to radiation.

DETAILED DESCRIPTION OF THE INVENTION

Various embodiments of the present invention relate to implantable medical devices, such as a stents, made from crosslinked bioabsorbable polymers. The embodiments further relate to methods of making the devices that include crosslinking the bioabsorbable polymer through radiation exposure. The embodiments are generally applicable to any tubular polymeric implantable medical device. In particular, the methods can be applied to tubular implantable medical devices such as self-expandable stents, balloon-expandable stents, and stent-grafts.

Figure 1:
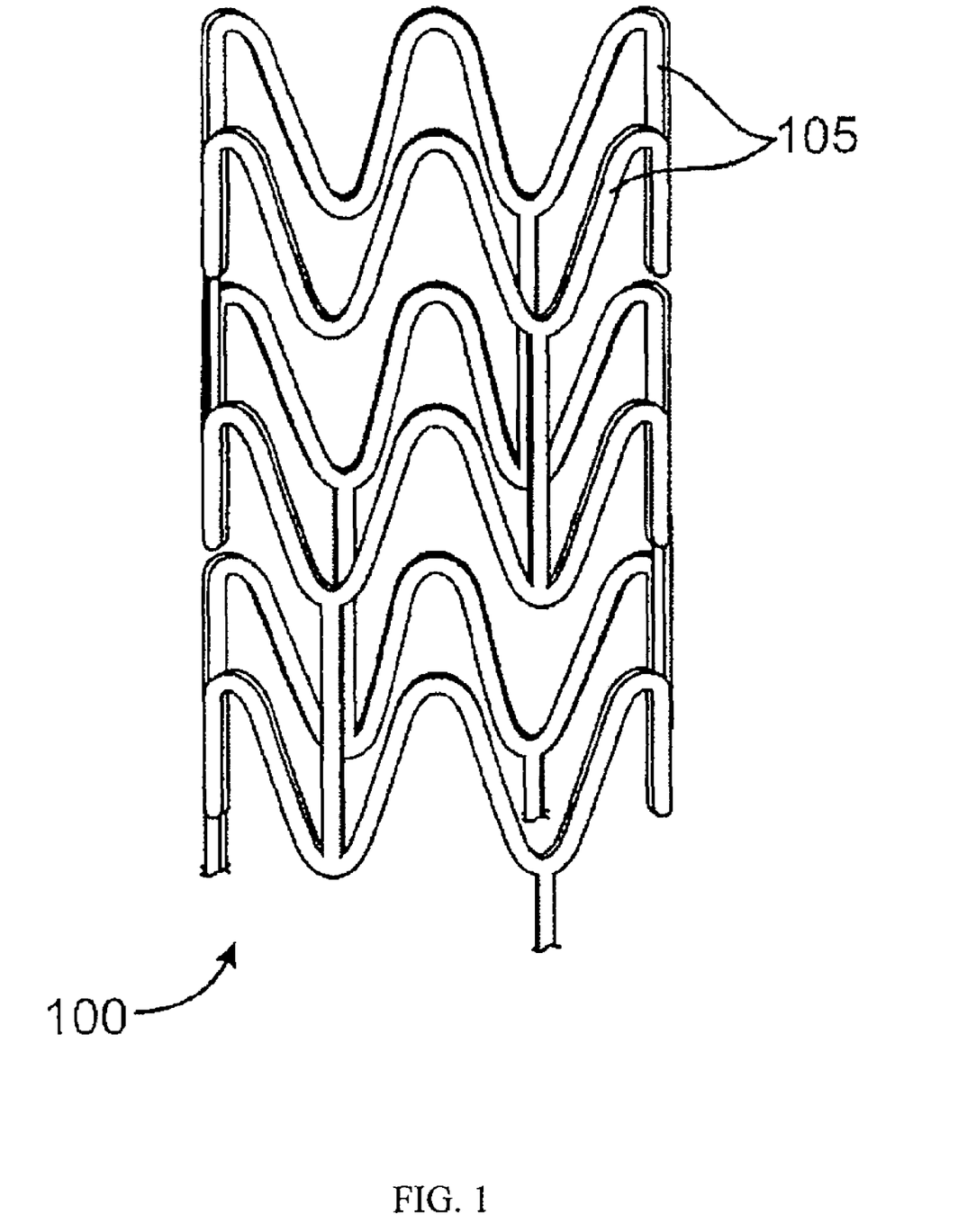
FIG. 1 depicts a stent.

A stent may include a pattern or network of interconnecting structural elements or struts. FIG. 1 depicts a view of a stent 100. In some embodiments, a stent may include a body, backbone, or scaffolding having a pattern or network of interconnecting struts or structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser machining or chemical etching.

A stent such as stent 100 may be fabricated from a polymeric tube or a sheet by rolling and bonding the sheet to form the tube. A tube or sheet for making a stent is conventionally formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The duration of a treatment period depends on the bodily disorder that is being treated. In treatments of coronary heart disease involving use of stents in diseased vessels, the duration can be in a range from about a month to a few years. However, the duration is typically up to about six months, twelve months, eighteen months, or two years. In some situations, the treatment period can extend beyond two years. The stent is expected to be completely degraded away from the vessel at the end of the treatment period.

As indicated above, a stent has certain mechanical requirements such as high radial strength, high modulus, high fracture toughness, and high fatigue resistance. A stent that meets such requirements greatly facilitates the delivery, deployment, and treatment of a diseased vessel. A polymeric stent with inadequate mechanical properties can result in mechanical failure or recoil inward after implantation into a vessel.

With respect to radial strength, the strength to weight ratio of polymers is usually smaller than that of metals. To compensate for this, a polymeric stent can require significantly thicker struts than a metallic stent, which can result in an undesirably large profile.

Additionally, polymers that are sufficiently rigid to support a lumen at conditions within the human body may also have low fracture toughness since they may exhibit a brittle fracture mechanism. For example, these include polymers that have a glass transition temperature (Tg) above human body temperature (Tbody), which is approximately 37° C. Such polymers may exhibit little or no plastic deformation prior to failure. It is important for a stent to be resistant to fracture throughout the range of use of a stent, i.e., crimping, delivery, deployment, and during a desired treatment period. PLLA is but one example of the class of semicrystalline polymers for which the above description is true. The Tg of PLLA has been reported to vary between approximately 55 and 65° C. Medical Plastics and Biomaterials Magazine, March 1998.

Certain embodiments of the present invention include a stent having a stent body made from a crosslinked bioabsorbable polymer. Embodiments can include generally a device body made from the crosslinked bioabsorbable polymer. Additionally, embodiments of the present invention further include making the stent body, or more generally, the device body. Embodiments of the method can include forming a construct, such as a tube that includes a bioabsorbable polymer. The bioabsorbable polymer may be uncrosslinked. Alternatively, the bioabsorbable polymer may already have some crosslinks. The bioabsorbable polymer of the construct becomes crosslinked when exposed to radiation. The bioabsorbable polymer may be exposed to radiation sufficient to crosslink the bioabsorbable polymer.

In exemplary embodiments, the bioabsorbable polymer can be a homopolymer or a copolymer. The bioabsorbable polymer can also be a polymer blend of two or more different types of polymer, either a miscible polymer blend or an immiscible polymer blend. The crosslinking in a polymer blend may result linking or bonding between polymers of different types. Alternatively, the crosslinking can be selective, in that only one type of polymer is crosslinked or only certain types of polymers are crosslinked in the blend.

Exemplary bioabsorbable polymers include poly(L-lactide) (PLLA), poly(D-lactide) (PDLA), polyglycolide (PGA), polymandelide (PM), polycaprolactone (PCL), poly(trimethylene carbonate) (PTMC), polydioxanone (PDO), poly(4-hydroxy butyrate) (PHB), and poly(butylene succinate) (PBS), poly(DL-lactide) (PDLLA), and poly(L-lactide-co-glycolide) (PLGA). Polymers that are preferred for a stent body are those that have thermal stability in the range at or close to Tbody, since such polymer may be rigid and maintain a high modulus and compressive strength at Tbody so that the stent can support a lumen. Such polymers have a Tg above human body temperature, preferably at least 10, 20, or 30° C. greater than human body temperature. PLLA and PLGA are examples of such polymers.

In additional embodiments, the bioabsorbable polymer can also be a blend of PLLA and PDLA to create a stereocomplex, which is expected to further enhance the thermal and mechanical stability of the polymer. Exemplary blends can have a ratio of PDLA to PLLA of between 0 and 1, although the blends can have a ratio greater than one.

The degree of crosslinking may be characterized by crosslink or crosslinking density. The crosslink density can be expressed as the average molecular weight (number average or weight average) between crosslink sites (Mc). Alternatively, the crosslink density can be expressed as the mole fraction of monomer units which are crosslink points (Xc). *An Introduction to Plastics*, Hans-Georg Elias $2^{nd}$ ed. Wiley (2003). Crosslink density, the molecular weigh between crosslinks (Mc), can be determined by known methods such as dynamical mechanical analysis (DMA).

The crosslink density can further be described as gel fractions. The gel fraction is calculated by the amount of insoluble material in solvent, when the crosslinked polymer is mixed with a solvent for the uncrosslinked polymer, with the following equation:

$$\text{Gel fraction (\%)} = (W_g/W_0)100$$

where $W_0$ and $W_g$ are the dried weights of the initial polymer and its remaining weight (the gel component which corresponds to the crosslinked component) after dissolution in a solvent at room temperature. When a crosslinked polymer is mixed into a solvent, a portion which is sufficiently crosslinked swells rather than dissolves in the solvent. A portion which is not crosslinked or not sufficiently crosslinked dissolves in the solvent. Therefore, the crosslinked portion may be separated from the remainder of the polymer so that a gel fraction provides a measure of the degree of crosslinking.

In embodiments of the present invention, the crosslink density of the crosslinked bioabsorbable polymer of the stent body can be determined from a number of techniques including equilibrium swelling (also known as degree of swelling), NMR spectroscopy, dynamic mechanical analysis, and gel fraction. Gel fraction is typically used and should be at least 1%. Sometimes, crosslink density and gel fraction are used interchangeably since gel fraction is related to crosslink density. For the purposes of this disclosure, these terms will be used interchangeably. The crosslink density of the bioabsorbable polymer of the tube after radiation exposure as determined by its gel fraction is increased by at least 1%. More specifically, the gel fraction is or is increased to between 1-5%, 5-20%, 20-50%, 50-70%, or greater than 70%.

Additionally, embodiments of the present invention further include making the stent body, or more generally, the device body. Embodiments of the method can include forming a construct, such as a tube that includes a bioabsorbable polymer. The bioabsorbable polymer of the construct is crosslinked when exposed to radiation.

As described in more detail below, the crosslinking can be caused or induced partially or completely by the presence of a crosslinking agent mixed or dispersed within the polymer. Alternatively or additionally, the crosslinking can be caused or induced by chemical reaction and bonding between reactive moieties present on different polymer chains of the bioabsorbable polymer. In this alternative, the crosslinking is bonding between functional groups of the polymer without being linked or bonded by a crosslinking agent that is distinct or separate from the polymer prior to the crosslinking.

The crosslinked bioabsorbable polymer can result in a stent body with high strength sufficient to support a bodily lumen for a desired time period, with high fracture toughness, and with acceptable recoil after deployment (less than 10% of the deployed diameter). The crosslinked bioabsorbable polymer may have a relatively low crystallinity, for example, between 10-25%. A distinct advantage of a stent body made from a crosslinked bioabsorbable polymer is that the polymer can have a relatively low crystallinity (e.g., 10-25%) while providing sufficient radial strength to support blood a vessel (e.g., less than 10% recoil for at least 1-3 months) and yet have relatively high fracture toughness (e.g., few or no cracked structural elements upon deployment). The crystallinity can be greater than 25%, however, it is important that the degree of crosslinking or crosslink density is not high enough to cause brittle behavior that results in unacceptable fracture or failure during use of a stent.

In some embodiments, the tube is exposed to radiation which causes the crosslinking of the polymer. A stent body is made from the exposed and crosslinked tube. In other embodiments, a stent body is fabricated from the tube prior to radiation exposure and the stent body is exposed to the radiation to crosslink the bioabsorbable polymer.

The fabrication of a stent from a tube may include additional processing steps. In some embodiments, the polymer tube can be radially deformed or expanded, axially deformed, or both radially and axially deformed. The stent body can be formed from the radially deformed, axially deformed, or radially and axially deformed tube. The deformation tends to increase the strength and toughness of the polymer. In particular, the radial deformation tends to increase the radial strength of the tube. The increase in radial strength is believed to be due to the circumferential polymer chain orientation and an increase in crystallinity, both induced by the deformation. Both radial and axial deformation provide biaxial orientation of the polymer chains.

The radial deformation can be accomplished by a blow molding process. In such a process, the polymer tube is disposed within a cylindrical mold with a diameter greater than the polymer tube. The polymer tube is heated, preferably so that its temperature is above its Tg. The pressure inside of the tube is increased to cause radial expansion of the tube so the outside surface of the tube conforms to the inside surface of the mold. The polymer tube can be axially deformed by a tensile force along the tube axis before, during, and/or after the radial deformation. The polymer tube is than cooled below Tg and further processing steps can then be performed, such as laser machining of the tube to form a stent pattern.

The degree of radial expansion or deformation may be quantified by percent radial expansion:

$$\left[\frac{\text{Outside Diameter of Deformed Tube}}{\text{Original outside Diameter of Tube}} - 1\right] \times 100\%$$

In some embodiments, percent radial expansion can be 200-500%. In an exemplary embodiment, the percent radial expansion is about 300%. Similarly, the degree of axial deformation may be quantified by the percent axial elongation:

Preliminary data suggests that 200 percent radial combined with 200% axial provides the best results.

$$\left[\frac{\text{Length of Deformed Tube}}{\text{Original Length of Tube}} - 1\right] \times 100\%$$

In some embodiments, the tube can be elongated before during or after the radial expansion. The percent axial elongation can be 30-100%.

In some embodiments, the tube is radially expanded prior to the exposing step and the stent body is formed from the expanded and exposed tube. Exposing the construct in the expanded state may be preferable since the crosslinking may tend to reduce or inhibit recoil and improve other physical properties, such as toughness.

In other embodiments including the radial expansion step, the tube can be crosslinked prior to the radial expansion step. In this embodiment, a stent body fabricated from an expanded tube may have a greater tendency to recoil toward the diameter of the tube prior to radial expansion. Recoil in this manner may be desirable for a treatment in which recoil from a deployed diameter is acceptable or desirable.

In another embodiment, there is no radial deformation step. In this embodiment, the polymer tube is exposed to radiation, followed by formation of a stent pattern. Alternatively, a stent pattern is formed in the tube, followed by radiation exposure. In either case, the stent may then be crimped. The crimped stent may then have a tendency to self-expand and can be deployed at an implant site through self-expansion rather than balloon expansion.

As indicated above, the stent body can be formed using laser machining to form a stent pattern in the tube. For example, a femtosecond laser can be used. Laser machining removes material of the tube to form the stent pattern. However, material not removed that is near a machined surface can be modified by energy from the laser. The modification is generally undesirable since mechanical properties are adversely effected. The modified region is referred to as a heat affected zone.

Another processing step can include forming a therapeutic coating layer over all or a portion of the stent body surface. The coating can include a therapeutic substance dispersed in a polymer.

A further processing step includes mounting the stent on a delivery device, for example, over a balloon on a catheter. The stent can be mounted by reducing the diameter of the stent with a crimping process so that the stent is secured to the balloon at a reduced diameter. In some embodiments, the stent body can be crosslinked at the crimped diameter. However, as mentioned above, the stent may have a strong tendency to recoil toward the crimped diameter. Such recoil may be undesirable in many treatment situations. However, recoil in this manner may be desirable for a treatment in which recoil from a deployed diameter is acceptable or desirable.

A further embodiment may be to treat the tube or stent with radiation after expansion, then crimp, and finally treat again with radiation for sterilization. The second sterilization dose may be low enough so that the crosslink density is not increased dramatically, so that recoil is not impaired.

In another embodiment, the tube or stent can be treated with radiation after expansion, then crimp, and sterilize with EtO.

In another embodiment, the tube or stent may be treated with radiation after extrusion, omit expansion, crimp, and finally sterilize with EtO.

A medical device, such as a stent, typically undergoes sterilization to reduce the bioburden of the stent to an acceptable sterility assurance level (SAL). Bioburden refers generally to the number of microorganisms with which an object is contaminated. SAL is a measure of the degree of sterilization and refers to the probability of a viable microorganism being present on a product unit after sterilization. There are numerous methods of sterilizing medical devices such as stents, the most common being ethylene oxide treatment and treatment with ionization radiation such as electron beam and gamma radiation. Generally, it is desirable for the sterilization procedure to have little or no adverse affects on the material properties of the stent. Stents are typically sterilized in a crimped state after packaging.

Ethylene oxide ("EtO") sterilization is performed by exposing the device to gaseous ethylene oxide mixtures at elevated temperatures, at high relative humidity for a period of time to obtain a desired bioburden level. The elevated temperatures (e.g., a temperature between 30° C. and (Tg−5° C.)) speeds up the sterilization of the device and the dissipation of the EtO from the device. Exposure to the EtO gas mixture can result in degradation of the mechanical properties of a polymer or distortion of the fabricated shape if the conditions are not chosen properly. The temperature, relative humidity, and time need to be chosen carefully to be compatible with the polymer. If any of the conditions are too high, the polymer can lose its intended shape, form, or function as the EtO, temperature, relative humidity, and time can affect these properties. An acceptable range may be 30° C. to 50° C., 30 to 100% relative humidity, with the lowest possible temperature and humidity preferred for PLLA. A radiation crosslinked stent would be more resistant to physical property, form, function and shape degradation after exposure to EtO sterilization conditions. Radiation sterilization is well known to those of ordinary skill the art. Medical devices composed in whole or in part of polymers can be sterilized by various kinds of radiation, including, but not limited to, electron beam (e-beam), gamma ray, ultraviolet, infra-red, ion beam, x-ray, and laser sterilization. A sterilization dose can be determined by selecting a dose that provides a required SAL. A sample can be exposed to the required dose in one or multiple passes.

However, it is known that radiation can alter the properties of the polymers being treated by the radiation. Such radiation can cause a drastic drop in molecular weight of the polymer due to chains scission and formation of free radicals. This can lead to a more brittle material prone to cracking during deployment (expansion). Sterilization occurs after crimping.

The present invention reduces or prevents the degradation or drastic drop in molecular weight of the polymer of a device caused by processing conditions which cause such degradation. In particular, the reduction in molecular weight and properties caused by sterilization are reduced or prevented by the crosslinking.

Additionally, the fracture toughness of the bioabsorbable polymer can be enhanced by the crosslinking since the crosslinking reduces the degree of crystallinity. Quynh, Tran et al., European Polymer Journal 43 1779-1785 (2007). Specifically, fracture toughness is enhanced if the crosslinking is sufficiently high, but can be reduced if the crosslinking is to high. Thus, if the radiation dose is not sufficiently high to induced the sufficient degree of crosslinking, the fracture toughness will not be enhanced. Also, if the radiation dose is too high, a degree of crosslinking can be induced that results in brittle behavior. Furthermore, the degree of crystallinity of a stent produced by the several possible crosslinking processes described above is lower than one that is not crosslinked. Thus, it is expected that cracking during crimping and deployment of the stent will be reduced or eliminated. Additionally, the crosslinking is expected to reduce the physical aging of the polymer since the degrees of freedom in the mobility of the polymer chains in reduced in the amorphous regions.

Furthermore, the crosslinking is also expected to enhance the thermal and mechanical stability of the polymer. The crosslinking tends to increase the Tg and increase the modulus. Thus, the recoil at Tbody is reduced.

Additionally, the stent may be sterilized using EtO, which may be more desirable than radiation since EtO may better preserve the properties of the finished good, i.e., the stent and catheter assembly. It has been observed in practice that EtO sterilization cycles tend to cause bioabsorbable stents to fracture upon deployment if the stents are not crosslinked.

As used herein, crosslinks refer generally to chemical covalent bonds that link one polymer chain to another. A crosslinked polymer includes crosslinks throughout a polymer material sample. When polymer chains are linked together by crosslinks, they lose some of their ability to move as individual polymer chains, thus stabilizing the polymer.

Crosslinks can be formed by chemical reactions that are initiated by heat, pressure, crosslinking agent, or radiation. The radiation can include, but is not limited to, electron beam, gamma, or UV light. The crosslinking induced by radiation can be caused by or facilitated by a crosslinking agent. A crosslinking agent is a substance or compound that promotes or regulates intermolecular covalent bonding between polymer chains, linking them together to create a more rigid structure. The crosslinking agent is a compound that is separate and distinct from the polymer chains prior to the crosslinking between which it promotes or regulates bonding. In its role in promoting or regulating covalent boding, the crosslinking agent becomes covalently bonded to the polymer chains. Therefore, the crosslinking agent can become incorporated into the crosslinked polymer.

Radiation crosslinking of polylactic acids with crosslinking agents has been described, for example, in Mitomo, Hiroshi et al., Polymer 46 4695-4703 (2005); Quynh, Tran et al., European Polymer Journal 43 1779-1785 (2007); and Quynh, J. of Applied Polymer Science, 110, 2358-2365 (2008), which are all incorporated by reference herein. The radiation dose, type, and mole or weight percent of a crosslinking agent can also influence the crosslink density. The radiation dose is directly proportional to the crosslink density.

In certain embodiments of the invention, the polymer construct that is to be irradiated, such as a tube, can include a crosslinking agent. The crosslinking agent can be mixed or dispersed within the bioabsorbable polymer of the tube. When the tube is exposed to radiation, the crosslinking agent induces crosslinking of the bioabsorbable polymer.

As already indicated, the degree of crosslinking depends on the weight percent of the crosslinking agent and the radiation dose. The tube may include an amount of crosslinking agent sufficient to provide a desired crosslink density or gel fraction. In exemplary embodiments, the tube includes less than 1 wt %, 1-3 wt %, 3-5 wt %, or greater than 5 wt % crosslinking agent. The remaining material of the tube can be the bioabsorbable polymer or consist essentially of the bioabsorbable polymer. The tube can also include a filler material mixed with the bioabsorbable polymer and crosslinking agent.

A limiting factor on the radiation dose and amount of crosslinking agents is that the crosslink density should not be so high that the bioabsorbable exhibits brittle fracture behavior during use of the stent, e.g., during crimping and deployment. Additionally, the concentration of crosslinking agent in the polymer can become so high that the performance and properties of bioabsorbable polymer are compromised. Thus, in general, the weight percent of crosslinking agent is preferably below 5 wt %. However, there may be polymer, crosslinking agent, and radiation dose combinations in which concentrations above 5 wt % that would be favorable.

The amount of crosslinking agent and radiation dose can be varied to obtain a desired crosslink density and gel fraction. Also, the amount of crosslinking agent and radiation dose can be varied to obtain desire mechanical properties such as high radial strength and high fracture toughness. The radiation dose can be 10-100 kGy, 30-40 kGy, or more narrowly 25-30 kGy. Exemplary crosslinking agents include triallyl isocyanurate (TAIC), trimethally isocyanurate (TMAIC), and trimethylolpropane triacrylate (TMPTA), however, other crosslinking agents may be used.

A crosslinking agent can be mixed or dispersed into the bioabsorbable polymer of a tube using melt processing. For example, the crosslinking agent can be fed into an extruder that in the manufacture of the tube. Alternatively, the crosslinking agent can be mixed with a polymer melt in batch and fed into a extruder or injection molder to make the tube. For example, the structure of TAIC is:

Although other crosslinking mechanisms are possible, the mechanism of the crosslinking can include chain scission induced by radiation between a C—C bond in the bioabsorbable polymer, such as PLLA, which contains a carbonyl and methyl group, but can occur elsewhere as well. During chain scission, a free radical is formed. The site of the free radical can then react with the C's of the double bond of the TAIC to form a saturated C—C crosslink.

The most effective crosslinking agent based on the magnitude of the gel fraction can be determined by measuring gel formation at various radiation dose levels. It has been found that TAIC is the most effective crosslinking agent in PLLA since it exhibits the highest gel fraction for radiation doses between 20 and 100 kGy at 3 wt % for each crosslinking agent. Mitomo, Hiroshi et al., Polymer 46 4695-4703 (2005). Likewise, the most effective concentration for a given crosslinking agent based on the magnitude of the gel fraction can be determined by measuring gel formation at various concentration levels and radiation doses. It has been found that a concentration of 3 wt % TAIC is the most effective in PLLA since it provides the highest gel fraction based on a comparison of concentrations between 0.5 wt % and 5 wt %. Mitomo, Hiroshi et al., Polymer 46 4695-4703 (2005)

Additionally, the concentration of crosslinking agent and radiation dose can be selected based on mechanical properties such as tensile strength and elongation at break (a measure of the fracture toughness of the polymer). It has been shown for irradiated PLLA containing TAIC samples that the tensile strength was the highest for 30 kGy dose compared to other doses between 0 and 50 kGy. Id. Additionally, it has been found that for a PLLA/PDLA blend with a 1:1 ratio of the polymers containing TAIC, the blend with the concentration of 3 wt % TAIC showed the best mechanical properties over a range of doses between 30 and 100 kGy.

A given radiation dose results in a corresponding degree of crosslinking. It may be desirable to minimize the residual unreacted crosslinking agent present in the finished stent. Therefore, in some embodiments, the amount of crosslinking agent in the tube prior to crosslinking can be selected so that all or substantially all of the crosslinking agents reacts to form the crosslinks.

Alternatively, the amount of crosslinking agent can be selected so that unreacted crosslinking agent remains in the bioabsorbable polymer after radiation exposure. When the stent is exposed to radiation in a sterilization step, additional crosslinking will occur which can further reduce or completely deplete the remaining crosslinking agent. This can be advantageous since the crosslinking reaction inhibits undesirable chains scission caused by radiation. Quynh, J. of Applied Polymer Science, 110, 2358-2365 (2008).

In further embodiments of the invention, the polymer construct that is to be irradiated, such as a tube, can be composed in whole or in part of a polymer that is crosslinkable due to formation of links or bonds between different moieties or functional groups of the polymer, referred to as a self-crosslinkable polymer, when exposed to radiation. In such embodiments, the polymer crosslinks form in the absence of a crosslinking agent. In some embodiments, the polymer is free of crosslinking agents that are not chemically bound to the polymer chains. The crosslinking can be due entirely to crosslinking between the moieties or functional groups of the polymer. In other embodiments, the polymer can additionally include a crosslinking agent so that crosslinking is due to the crosslinking agent and the reaction between the moieties or functional groups of the polymer without the aid of the crosslinking agent.

In some embodiments, the self-crosslinkable polymer can be a copolymer that includes reactive functional groups, for example, alkenes or alkynes, and functional groups that form biodegradable polymers when polymerized or copolymerized. The latter functional groups (referred to as degradable functional groups) are derived from monomers that include, but are not limited to L-lactic acid, glycolic acid, caprolactone, dioxanone, D-lactic acid, mandelic acid, trimethylene carbonate, 4-hydroxy butyrate, and butylene succinate. "Reactive" refers to upon exposure of the polymer to radiation, crosslinking is induced at the reactive functional groups.

The self-crosslinkable polymer can be formed through copolymerization of compounds that have the reactive functional groups and a monomer, such as lactic acid, to form a biodegradable, crosslinkable polymer. The self-crosslinkable copolymer can be a random or alternating copolymer.

Although other crosslinking mechanisms are possible, the mechanism of the crosslinking of the self-crosslinkable polymer can include chain scission induced by radiation between a C—C bond in a degradable functional groups, such as lactic acid, which contains carbonyl and the methyl group, but can occur elsewhere as well. During chain scission, a free radical is formed. The site of the free radical can then react with a reactive site of the highly reactive functional groups to form a C—C crosslink.

Although other types of reactive functional groups are possible, in some embodiments, the reactive functional groups include alkenes or alkynes. The double or triple bonds of the alkene or alkyne, respectively, act as the reactive sites that form crosslinks with the degradable functional groups. In particular, the site of the free radical can then react with the alkene to form a saturated C—C crosslink or react with the alkyne to form a C—C crosslink with a double bond.

In such embodiments, the bioabsorbable polymer is a copolymer formed through copolymerization of one or more monomers, such as lactic acid, with an alkene or alkyne. A general form of such a self-crosslinkable copolymer is AxBy, where A is a moiety such as lactic acid, and B is an alkene or alkyne that can copolymerize with A, and where x is the mole % of A and y is the mole % of B in the copolymer. Exemplary compositions can include x as 90-96 wt % and y as 4-10 wt %, although x and y can be outside these ranges.

For example, a self-crosslinkable polymer formed from L-lactide and a-allyl-δ-valerolactone is:

Additionally, a self-crosslinkable polymer formed from L-lactide and a-alkyne-δ-valerolactone is:

In exemplary embodiments, the reactive functional groups can include lactones with alkene or alkyne groups. Exemplary alkene monomers that can be copolymerized with a monomers such as lactic acid to form a self-crosslinkable polymer include, but are not limited to, a-allyl-δ-valerolactone (AVL) or a-allyl-ε-caprolactone. Exemplary alkyne monomers that can be copolymerized with a monomer such as lactic acid to form a self-crosslinkable polymer including, but are not limited to, a-alkyne-δ-valerolactone or a-alkyne-ε-caprolactone. δ-valerolactone can be converted to a-alkene-δ-valerolactone or a-alkyne-δ-valerolactone. Similarly, δ-caprolactone can be converted to a-alkene-δ-valerolactone or a-alkyne-δ-valerolactone. The copolymers named above are all random copolymers.

Schemes for functionalizing lactones with allyl and alkyne groups have been disclosed. Parrish, Bryan et al., J. of Polymer Science: Part A: Polymer Chemistry, Vol. 40, 1983-1990 (2002) and Parrish, Bryan et al., J. Am. Chem. Soc., 127, 7404-7410 (2005), which are incorporated by reference herein. Lactones can be functionalized with allyl groups α to the carbonyl as intermediates. This a methylene group is susceptible to functionalization under anionic conditions because of the enhanced acidity of its protons relative to the other protons on the ring. For example, δ-valerolactone can be functionalized with an allyl to form a-allyl-δ-valerolactone according to the following scheme (Id.):

The δ-valerolactone is quenched with allyl bromide/HMPA. Similarly, δ-valerolactone can be functionalized with an alkyne to form a-alkyne-δ-valerolactone according to the following scheme (Id.):

Both the alkene and alkyne have high thermal stability, with the alkene being more thermally stable than the alkyne. The high thermal stability allows processing with reduced or no degradation through conventional melt processing, such as extrusion.

A copolymer of the functionalized lactone and a degradable functional group, such as L-lactic acid, may be synthesized according to the following exemplary reaction between L-lactic acid and a-allyl-δ-valerolactone to form poly(L-lactide-co-a-allyl-δ-valerolactone) (poly(LLA-co-AVL):

Additionally, the self-crosslinkable polymer can be a copolymer of α,α-diallyl-δ-valerolactone (DAVL) and a degradable functional group, such as L-lactic acid. DAVL can be synthesized as follows:

L-lactic acid and DAVL are copolymerized to form poly(LLA-co-DAVL) as follows:

In other embodiments, a self-crosslinkable polymer can be made through a scheme including a transesterification reaction between a degradable polyester, such as PLLA, and a diol like PEG or a triol such as 1,1,1-tris(hydroxymethyl)ethane. Then a chain extension is conducted with the degradable polymer and an alkyne such as glycidyl propargyl ether or alkyne valerolactone. For example, a transesterification of PLLA and a diol like 1,1,1-tris(hydroxymethyl)ethane can be performed as follows:

The chain extension with the PLLA and an alkyne such as glycidyl propargyl ether or alkyne valerolactone is as follows:

In the structure above, the pendant groups containing the red dots represent alkyne or alkene functional groups. The alkyne monomers, glycidyl propargyl ether and alkyne valerolactone, respectively, are shown below:

The body, scaffolding, or substrate of a stent may be primarily responsible for providing mechanical support to walls of a bodily lumen once the stent is deployed therein. A stent body, scaffolding, or substrate, for example, as pictured in FIG. 1, can refer to a stent structure with an outer surface to which no coating or layer of material different from that of which the structure is manufactured. If the body is manufactured by a coating process, the stent body can refer to a state prior to application of additional coating layers of different material. "Outer surface" refers to any surface however spatially oriented that is in contact with bodily tissue or fluids. A stent body, scaffolding, or substrate can refer to a stent structure formed by laser cutting a pattern into a tube or a sheet that has been rolled into a cylindrical shape.

In some embodiments, the stent body, scaffolding, struts, or structural elements of the present invention may be nonporous or substantially nonporous. Substantially nonporous refers to a porosity of less than 0.1 percent. Alternatively, the stent body, scaffolding, struts, or structural elements of the present invention may be porous. Additionally, the surface of the stent body, scaffolding, struts, or structural elements of the present invention may have cavities or alternatively, be cavity-free.

For the purposes of the present invention, the following terms and definitions apply:

"Molecular weight" can refer to the molecular weight of individual segments, blocks, or polymer chains. "Molecular weight" can also refer to weight average molecular weight or number average molecular weight of types of segments, blocks, or polymer chains.

The number average molecular weight (Mn) is the common, mean, average of the molecular weights of the individual segments, blocks, or polymer chains. It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi.

"Ambient temperature" can be any temperature including and between 20° C. and 30° C.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Other representative examples of polymers that may be used to fabricate an implantable medical device include, but are not limited to, poly(N-acetylglucosamine) (Chitin), Chitosan, poly(hydroxybutyrate), poly(hydroxybutyrate-co-valerate), polyorthoester, polyanhydride, polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

EXAMPLES

Some embodiments of the present invention are illustrated by the following examples. The examples are being given by way of illustration only and not by way of limitation. The parameters and data are not be construed to unduly limit the scope of the embodiments of the invention.

Example 1

Synthesis of poly(L-lactide-co-a-allyl-δ-valerolactone) (poly(LLA-co-AVL) was performed according to the reaction scheme described above. All reactions were performed with 0.04 mol % Sn(Oct)2 catalyst. Details of the synthesis and molecular weight data are provided in Table 1.

TABLE 1

Poly(LLA-co-AVL) composition and molecular weight analysis.

| Reaction Time [h] | Yield [%] | Feed [mol %] AVL:LLA | Incorp. AVL[a] [mol %] | Mn[b] | Mw[b] | PDI[b] |
|---|---|---|---|---|---|---|
| 1a | 17 | 38 | 0:100 | — | 67k | 109k | 1.63 |
| 1b | 18 | 37 | 0:100 | — | 122k | 221k | 1.81 |
| 2 | 15 | 68 | 5:95 | 1.4 | 74k | 125k | 1.70 |
| 3 | 15 | 75 | 10:90 | 2.6 | 61k | 135k | 2.20 |
| 4a | 20 | 48 | 20:80 | 3.9 | 69k | 115k | 1.65 |
| 4b | 20 | 73 | 20:80 | 3.7 | 129k | 194k | 1.51 |
| 5 | 20 | 55 | 30:70 | 5.6 | 82k | 124k | 1.43 |

[a]Determined by 1H-NMR,
[b]Determined by GPC in CHCl3 using Polystyrene standards, Molecular weight in g/mole, PDI = polydispersity index.

Samples of poly(LLA-co-AVL) were prepared with different mole percentages of AVL. The samples were analyzed with dynamic scanning calorimetry (DSC) to determine the Tg and the melting temperature (Tm). The results of the DSC analysis are shown in Table 2.

TABLE 2

Tg and Tm from DSC for different mole percentages of AVL in poly(LLA-co-AVL).

| | Mol % AVL in PLLA | | | | |
|---|---|---|---|---|---|
| | 0 | 1.4 | 2.6 | 3.9 | 5.6 |
| Tg [° C.] | 61 | 59 | 58 | 52 | 48 |
| Tm [° C.] | 175 | 160 | 164 | 159 | 150 |

Example 2

Synthesis of poly(L-lactide-co-a α,α-diallyl-δ-valerolactone) (poly(LLA-co-DAVL) were performed according the to reaction scheme described above. All reactions were performed with 0.04 mol % Sn(Oct)2 catalyst. The reactions for samples 1 and 2 were performed without an initiator. Details of the synthesis and molecular weight data are provided in Table 3.

TABLE 3

Poly(LLA-co-AVL) composition and molecular weight Analysis.

| Reaction Time [h] | Yield [%] | Feed [mol %] DAVL:LLA | Incorp. DAVL [mol %] | Mn[b] | Mw[b] | PDI[b] |
|---|---|---|---|---|---|---|
| 1 | 18 | 57 | 10:90 | 0.6 | 82k | 143k | 1.73 |
| 2 | 18 | 39 | 20:80 | 0.6 | 60k | 111k | 1.87 |
| 3 | 17 | 45 | 30:70 | — | 49k | 81k | 1.64 |

[a]Determined by 1H-NMR,
[b]Determined by GPC in CHCl3 using polystyrene standards.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a stent, comprising:
   forming a tube comprising a bioabsorbable polymer, wherein the bioabsorbable polymer crosslinks when exposed to radiation;
   exposing the bioabsorbable polymer to radiation sufficient to crosslink the bioabsorbable polymer; and
   forming a stent body from the exposed tube comprising the crosslinked bioabsorbable polymer.

2. The method of claim 1, further comprising sterilizing the stent body through exposure to radiation, wherein the crosslinking reduces or prevents molecular weight degradation of the bioabsorbable polymer due to the sterilizing radiation.

3. The method of claim 1, further comprising sterilizing the stent body with ethylene oxide at an elevated temperature above 30° C., wherein the crosslinking reduces or prevents mechanical property degradation of the bioabsorbable polymer due to the deleterious effect of EtO, humidity, and the elevated temperature of the ethylene oxide sterilization.

4. The method of claim 1, wherein the radiation comprises e-beam radiation.

5. The method of claim 1, wherein the radiation comprises γ (gamma) radiation.

6. The method of claim 1, further comprising radially expanding the tube prior to the exposing step, wherein the stent body is formed from the expanded and exposed tube.

7. The method of claim 1, wherein the tube comprises a crosslinking agent that induces the crosslinking of the bioabsorbable polymer when the tube is exposed to the radiation.

8. The method of claim 1, wherein the tube comprises TAIC which induces crosslinking of the bioabsorbable polymer when the tube is exposed to the radiation.

9. The method of claim 8, wherein the wt % of TAIC in the tube is 0.5-5%.

10. The method of claim 1, wherein the radiation exposure is 20-40 kGy.

11. The method of claim 1, wherein the bioabsorbable polymer comprises PLLA or a blend of PLLA and PDLA which forms a stereocomplex.

12. The method of claim 1, wherein the bioabsorbable polymer is crosslinkable due to formation of bonds between different functional groups of the bioabsorbable polymer when exposed to radiation, the crosslinking is bonding between the functional groups without being linked by a crosslinking agent that is distinct or separate from the bioabsorbable polymer.

13. The method of claim 1, wherein the bioabsorbable polymer is a copolymer formed through copolymerization of one or more types of degradable functional groups with a highly reactive functional group, wherein the one or more types of degradable functional groups form a degradable polymer when polymerized or copolymerized.

14. The method of claim 13, wherein the crosslinks comprise bonds between the highly reactive functional groups and the degradable functional groups.

15. The method of claim 13, wherein the highly reactive functional groups comprise an alkene or alkyne.

16. The method of claim 13, wherein the highly reactive functional groups comprise a lactone functionalized with an alkene or an alkyne group.

17. The method of claim 1, wherein the bioabsorbable polymer is a copolymer of the form AxBy, wherein A is L-lactic acid and B is an alkene or alkyne that can copolymerize with A, and wherein x is the mole % of A and y is the mole % of B in the copolymer.

18. The method of claim 17, wherein x is 90-96 wt % and y is 4-10 wt %.

19. The method of claim 17, wherein B is selected from the group consisting of a-allyl-δ-valerolactone, a-diallyl-δ-valerolactone, a-alkyne-δ-valerolactone, a-allyl-δ-caprolactone, a-diallyl-δ-caprolactone, and a-alkyne-δ-caprolactone.

20. The method of claim 1, wherein the bioabsorbable polymer is formed through a transesterification reaction between a degradable polyester and a diol or a triol followed by a chain extension conducted with the degradable polymer and an alkyne or alkyne.

21. The method of claim 20, wherein the degradable polyester is PLLA, the diol is PEG, the triol is 1,1,1-tris(hydroxymethyl)ethane, the alkene is glycidyl propargyl ether, and the alkyne is an alkyne valerolactone.

22. A method of fabricating a stent, comprising:
forming a tube comprising a bioabsorbable polymer, wherein the bioabsorbable polymer crosslinks when exposed to radiation;
forming a stent from the tube; and
exposing the stent to radiation sufficient to crosslink the bioabsorbable polymer,
wherein the bioabsorbable polymer is a polymer formed through a transesterification reaction between a degradable polyester and a diol or a triol followed by a chain extension conducted with the degradable polymer and an alkene or alkyne.

* * * * *